United States Patent [19]

Andreiko et al.

[11] Patent Number: 5,018,969
[45] Date of Patent: May 28, 1991

[54] BRAIDED ELASTIC WIRE, WITH MEMORY, FOR BRACES

[75] Inventors: Craig Andreiko, Alta Loma; Terry L. Sterrett, Long Beach, both of Calif.

[73] Assignee: Ormco Corporation, Glendora, Calif.

[21] Appl. No.: 411,646

[22] Filed: Sep. 25, 1989

[51] Int. Cl.⁵ .............................................. A61C 3/00
[52] U.S. Cl. .................................................... 433/20
[58] Field of Search ........................ 433/20; 420/417; 148/402

[56] References Cited

U.S. PATENT DOCUMENTS

| | | | |
|---|---|---|---|
| 3,123,913 | 3/1964 | Rubin | 433/20 |
| 4,182,106 | 1/1980 | Henry | 433/20 |
| 4,197,643 | 4/1980 | Burstone | 148/407 |
| 4,533,321 | 8/1985 | Kidd et al. | 433/11 |
| 4,818,226 | 4/1989 | Berendt et al. | 433/20 |

*Primary Examiner*—Cary E. Stone
*Attorney, Agent, or Firm*—Ellsworth R. Roston; Charles H. Schwartz

[57] ABSTRACT

A plurality of strands are disposed in a braided relationship to form a multi-strand filament. Each of the strands is formed from a material having substantially fifty five percent (55%) titanium and forty five percent (45%) nickel by weight. The strands have the properties of being formed to any desired configuration in an arched relationship at a suitable temperature such as approximately 490° C. The multi-strand configuration is then bent from the desired configuration at a temperature below a particular temperature such as 10° C.–15° C. to conform to the actual configuration of the teeth in the patient's mouth and is attached to the patient's teeth in this bent configuration. The multi-strand filament returns to the desired configuration while attached to the patient's teeth, thereby causing the position of the teeth in the patient's mouth to become disposed in the desired configuration. In another embodiment, the multi-strand braid envelopes a centrally disposed wire. The centrally disposed wire may be made from the same material as, or a different material than, the braids, depending upon the characteristics desired.

17 Claims, 2 Drawing Sheets

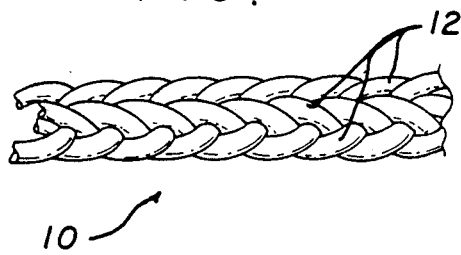
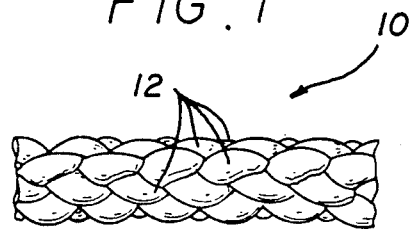
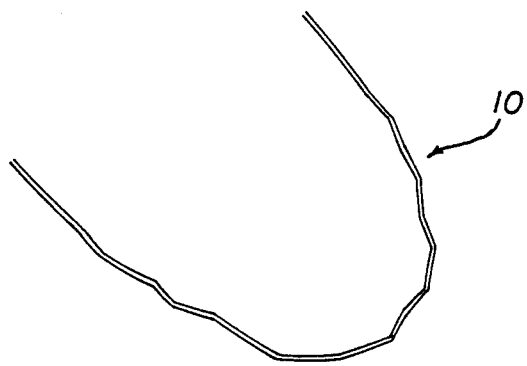
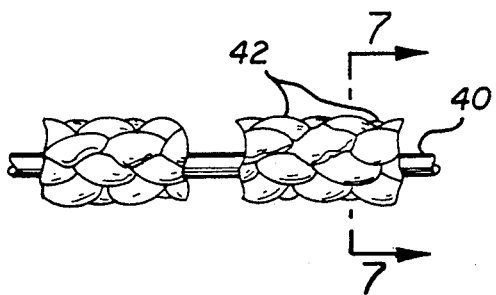
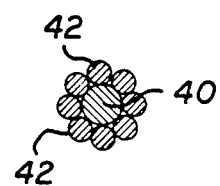

FIG. 4
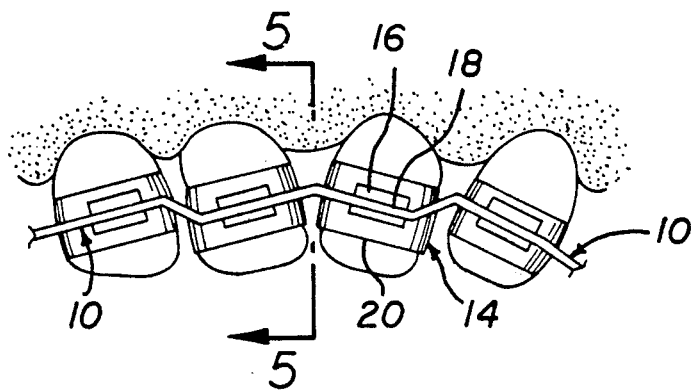
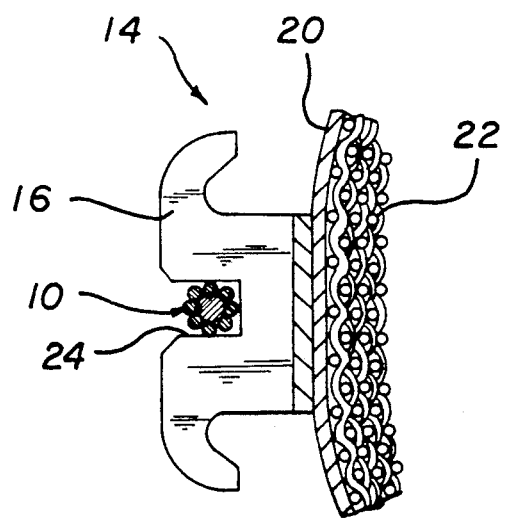
FIG. 5

BRAIDED ELASTIC WIRE, WITH MEMORY, FOR BRACES

This invention relates to a multi-strand filament for use in re-setting the position of teeth in a patient's mouth. More particularly, the invention relates to a multi-strand filament with properties of being pre-set to the desired configuration of teeth in a patient's mouth, of being bent to the actual configuration of such teeth in the patient's mouth and of re-setting the teeth in the patient's mouth to the desired configuration.

When the teeth in a patient's mouth are displaced from an even or uniform disposition, such displacements tend to produce problems over an extended period of time. For example, such displacements may produce problems in the patient's gums. These problems may cause the retention of teeth by the patient's gums to become weakened so that the teeth become loose in the patient's mouth. The problem may become so aggravated that the teeth may eventually have to be removed from the patient's mouth.

To prevent the conditions in a patient's mouth from deteriorating, dentists often attempt to reset the positions of the teeth in a patient's mouth. The dentists do this by attaching braces to the patient's teeth and by gradually adjusting the forces applied to the teeth. These forces act against the teeth in the patient's mouth to move the teeth gradually toward the positions desired by the dentist.

The techniques discussed in the previous paragraph have had some beneficial effect but they are expensive because they require a considerable amount of work by the dentist to progressively adjust the forces applied against the teeth. Furthermore, the results in the disposition of the teeth are not always as perfect as the dentist and the patient may desire because it is not easy for the dentist to move each tooth individually to the desired position.

In recent years, materials with a memory have been provided. These materials have been used as orthodontic arch wires to reduce the number of adjustments which have to be made by the dentist to reset the position of the teeth in the patient's mouth. Because of this memory, the othodontic arch wires can be formed to a configuration corresponding to the desired positioning of the teeth in the patient's mouth. The orthodontic arch wires can then be bent to the actual disposition of the teeth in the patient's mouth and can be attached to the teeth in this bent configuration. Because of the memory in the material of each orthodontic wire, the arch wire tries to move to its formed configuration and forces the position of the teeth in the patient's mouth to change accordingly. Such a wire is disclosed and claimed in U.S. Pat. No. 4,037,324 issued to George F. Andreasen on Jul. 26, 1979.

One problem with the orthodontic arch wires discussed in the previous paragraph is that the memory of the orthodontic arch wires is not as perfect as the dentist ordinarily desires. In other words, when the orthodontic arch wire is bent from a formed configuration to become attached to the brackets which are bonded to the teeth in the patient's mouth, it does not return to this formed configuration. This is particularly true when the material of the orthodontic arch wire is sharply bent. This prevents the orthodontic arch wire from resetting the teeth to the formed configuration. Furthermore, it is not always easy to bend such orthodontic arch wires from their formed configurations, particularly when the wires have to be sharply bent.

To ease the forces required to shape the orthodontic arch wire to the configuration of the teeth in a patient's mouth and to increase its resiliency, the arch wire has been typically formed into braids. For example, braided wires for othodontia are disclosed and claimed in U.S. Pat. No. 3,123,913 issued to James M. Rubin on Mar. 20, 1964. Other examples of braided orthodontic devices are disclosed in U.S. Pat. No. 4,533,321 issued to Patrick D. Kidd et al on Aug. 6, 1985. However, neither of these patents discloses or claims a material with a memory for use as the braids.

As will be seen from the above discussion, the complete solution to the problem has eluded persons skilled in the art for a long period of time even though a substantial effort has been made, and significant sums of money have been expended, to solve the problem. Although the use of braided wires for orthodontia purposes have been known for more than a quarter of a century, wires with memory have not been braided for orthodontia purposes. Furthermore, although wires with some memory have been known for almost fourteen (14) years, such wires have not been braided. Actually, in U.S. Pat. No. 4,037,024 which discloses a single wire for orthodontia purposes, a material including titanium, nickel and cobalt has been described as the preferred embodiment and this material has been described for providing only a single-strand wire.

In one embodiment of the invention, a plurality of strands are disposed in a braided relationship to form a multi-strand filament. Each of the strands is formed from a material having substantially fifty five percent (55%) titanium and forty five percent (45%) nickel by weight. The strands have the properties of being bent to any desired shape or configuration at a temperature below a particular temperature such as 10° C.–15° C. and of returning to the formed configuration at any temperature above the particular temperature.

The multi-strand filament is preferably formed at a suitable temperature such as approximately 490° C. to a configuration corresponding to the desired configuration of the teeth in a patient's mouth. The multi-strand configuration is then bent from the formed configuration at a temperature below a particular temperature such as approximately 10° C. -15° C. to conform to the actual configuration of the teeth in the patient's mouth and is attached to the patient's teeth in this bent configuration. The multi-strand filament returns to the desired configuration while attached to the patient's teeth, thereby causing the position of the teeth in the patient's mouth to become disposed in the desired configuration.

In another embodiment, the multi-strand braid envelopes a centrally disposed wire. The centrally disposed wire may be made from the same material as, or a different material than, the braids, depending upon the characteristics desired.

In the drawings:

FIG. 1 is a fragmentary view of a filament of eight (8) stands braided in a "one-on-one" relationship;

FIG. 2 is a fragmentary view of a filament, similar to that of FIG. 1, of eight (8) strands braided in a "two-on-one" relationship;

FIG. 3 is a perspective view of a braided filament, constructed as shown in FIG. 1 or FIG. 2, in a configuration corresponding to the desired positioning of the teeth in a patient's mouth;

FIG. 4 illustrates a portion of composite pads or bases constructed to receive the multi-strand filament of FIG. 3 in a patient's mouth;

FIG. 5 is a sectional view of one of the pads shown in FIG. 4 and is taken substantially on the line 5—5 of FIG. 4;

FIG. 6 is a fragmentary view of another embodiment of a multi-strand filament of this invention; and FIG. 7 is a schematic sectional view of the embodiment shown in FIG. 6 and is taken substantially on the line 7—7 of FIG. 6.

In one embodiment of the invention, a multi-strand filament or wire generally indicated at 10 is provided for orthodontia purposes. Each of the strands in the filament 10 is indicated at 12 and each is made from a material designated by the trademark "Nitinol" and comprising substantially fifty five percent (55%) titanium by weight and forty five percent (45%) nickel by weight. The "Nitinol" material used in this invention does not include any cobalt such as is included in the preferred embodiment in U.S. Pat. No. 4,037,324.

The strands 12 in the filament 10 may be braided in a conventional manner. For example, the strands 12 may be braided in a "two-on-one" relationship as in FIG. 2 or in a "one-on-one" relationship as in FIG. 1. Preferably a plurality of strands are used, at least three (3) strands being preferable. FIGS. 1 and 2 show embodiments with eight (8) strands. However, other numbers of strands, such as nine (9), may preferentially be used.

When used as the material in the multi-strand filament 10, "Nitinol" material with a composition of substantially fifty five percent (55%) titanium and forty five percent (45%) nickel certain important advantages. Below a critical temperature range such as approximately 10° C. to 15° C., the "Nitinol" material is quite ductile. This means that the material can be shaped in any desired configuration at temperatures below the critical temperature. The ductility of the material in this temperature range results from a martensitic shear wherein adjacent planes of atoms shift by a distance less than a full interatomic distance.

At temperatures above the critical temperature range, the Nitinol material of this invention retains the configuration applied to it at the suitable presetting temperature such as 490° C. When the filament 10 is defined by a plurality of strands 12 formed from the Nitinol material, the filament has a low modulus so that it can be bent relatively easily. Furthermore, when bent from the pre-set shape at temperatures below the critical temperature range, the filament 10 has the properties of returning to the shape pre-set above the critical temperature range. This is true even when the filament 10 is sharply bent. These characteristics do not exist in any other material in braided form for use in orthodontia.

The multi-strand filament 10 may be first pre-set in an arched configuration with a progressive curvature (and no discontinuities) by shaping the filament at a suitable temperature such as approximately 490° C. This is the curvature desired for the patient's teeth. When the multi-strand filament 10 is used for orthodontia, its temperature is first reduced to a temperature below the critical temperature. The filament 10 is then formed into a particular configuration (generally with discontinuities) as illustrated schematically in FIG. 3. This formed configuration preferably may have a parabolic shape (with discontinuities in the parabola as indicated schematically in FIG. 3) and conforms to the positioning of the teeth in a patient's mouth. The temperature of the filament 10 is then returned to ambient mouth temperature. At ambient mouth (above 10°–15° C.) temperature, the filament 10 has the properties of returning to the arched configuration with no discontinuities.

In order to attach the multi-strand filament 10 to the teeth, pads generally indicated at 14 are attached to the teeth. The pads 14 may be constructed as disclosed and claimed in U.S. Pat. No. 4,068,399 issued to Frank R. Miller, Craig A. Andreiko and Kenneth R. Premo on Jan. 17, 1978 and U.S. Pat. No. 4,165,561 issued to Frank R. Miller, Craig A. Andreiko and Kenneth R. Premo on Aug. 28, 1979. Each pad 14 includes a bracket 16 indented as at 18 at a central position to receive the multi-strand filament 10. The pads 14 may be provided with a surface 20. A mesh or screen 22 such as a stainless steel mesh may be bonded at opposite ends to the surface 20 and to one of the teeth in the patient's mouth. In this way, a plurality of the pads 14 may be attached to successive teeth in the patient's mouth and the multi-strand filament 10 may be extended through the indentations 18 in the brackets 16 in these pads. It will be appreciated that the pads 14 constitute only one type of member which can be used to support the multi-strand filament 10 and that other types of members can be used without departing from the scope of the invention.

When the teeth in the patient's mouth are displaced from the formed configuration (as indicated schematically in FIG. 3), the multi-strand filament becomes bent from the formed configuration when the filament becomes attached as by the brackets 18 to the successive teeth in the patient's mouth. This causes the multi-strand filament 10 to exert a force on the teeth in the patient's mouth to move the teeth to the formed configuration indicated schematically in FIG. 3. This force is instrumental over a period of time in displacing the teeth to positions corresponding to the formed configuration illustrated schematically in FIG. 3.

FIGS. 6 and 7 illustrate another embodiment of the invention. In this embodiment, a wire 40 is centrally disposed as a core and a braid 42 is wound on the wire 40. The braid 42 is preferably formed from eight (8) strands in a two-on-one relationship although the braid can be formed in other relationships such as with nine (9) strands. Although each braid and the wire 40 are illustrated as being circular in cross section, it will be appreciated that the braids and the wire may be provided with other configurations in cross section. The wire 40 may be solid or it may be hollow. Preferably the wire 40 is made from the same "Nitinol" material as described above for the braid. However, the wire 40 may be formed from other materials than "Nitinol". For example, the wire 40 may be formed from a stainless steel or from a material such as a titanium molybdenum alloy disclosed and claimed in U.S. Pat. No. 4,219,617.

The embodiment shown in FIGS. 6 and 7 has certain important advantages. For example, the characteristics of the wire 40 can be varied to control the stiffness. The stiffness of the material can be controlled by varying the thickness of the wire 40 and/or by varying the material of this wire. Even when the braid 42 is wound on the wire 40, the resiliency of this filament is significantly greater than the resiliencies of the filaments of the prior art.

The multi-strand filament 10 of this invention has certain important advantages over the prior art. It has a substantially perfect memory even when it is sharply bent. This means that it is able to displace teeth to a desired configuration in a patient's mouth without progressive adjustments by the dentist of the forces exerted on the teeth. This accordingly minimizes any discomfort which the patient experiences when the dentist has to adjust the forces on the teeth. It also minimizes the time for the teeth to be adjusted in position to the desired configuration.

The multi-strand filament 10 of this invention also has other important advantages. Since it is formed from strands, the multi-strand filament 10 with a particular cross-sectional area has a significantly greater resiliency, but less stiffness, than a solid wire formed from the same material and with the same cross-sectional area. The multi-strand filament 10 of this invention also has been found to have a significantly more perfect memory than a solid wire of the same material.

In view of its enhanced resiliency and low stiffness, the multi-strand filament 10 of this invention can be shaped very early in the treatment of malocclusions to substantially fill the groove 24 in the bracket 16. In this way, the resultant combination is able to gain control on the forces exerted on the maloccluded teeth in all three (3) planes of space while maintaining acceptable physiological levels of force from the initiation of treatment of the patient. The groove 18 can be substantially filled by making the external cross-sectional dimension of the braid substantially the same as that of a solid wire of the prior art.

In U.S. Pat. No. 4,037,324, a material formed from a combination of titanium, nickel and cobalt has been described as the preferred embodiment for orthodontia purposes when the material has been formed into a solid wire. In such a 1 combination, six and one half percent (6.5%) of the nickel by weight in the material has been replaced by cobalt. However, when used in the multi-strand filament 10, the material formed from substantially fifty percent (55%) titanium and forty five percent (45%) nickel by weight has been found signicantly superior from the standpoint of memory retention than the material formed from the combination of titanium, nickel and cobalt.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

We claim:

1. In combination for resetting the position of teeth in a patient's mouth to a particular configuration,
a plurality of strands made from a material having a composition of substantially fifty five percent (55%) titanium and forty five percent (45%) nickel,
the plurality of strands being disposed in a braided relationship to define a filament,
the multi-strand filament having properties of being formed to the particular configuration at a particular elevated temperature for disposition in a patient's mouth, of being bent easily to any other configuration than the particular configuration at a critical temperature below the particular elevated temperature in accordance with the disposition of the teeth in the patient's mouth, of being coupled to the patient's teeth in such other configuration and of returning to the particular configuration at a temperature above the critical temperature.

2. In a combination as set forth in claim 1 wherein the strands are braided in a two-over-one mode.

3. In a combination as set forth in claim 1 wherein the strands are braided in a one-over-one mode.

4. In a combination as set forth in claim 1 wherein there are at least three (3) strands in the filament.

5. In a combination as set forth in claim 1,
wherein the other configuration corresponds to the configuration of the teeth in the patient's mouth.

6. In combination for resetting the position of teeth in a patient's mouth to a particular configuration,
a plurality of strands disposed in a braided relationship to form a multi-strand filament, each of the strands being formed from a material having substantially fifty five percent (55%) titanium and forty five (45%) nickel by weight,
the multi-strand filament having properties of being formed at a particular elevated temperature to the particular configuration, of being bent from the particular configuration at a critical temperature below the particular temperature in accordance with the actual disposition of the teeth in the patient's mouth, of being attached to the patient's teeth in the bent configuration and of returning to the particular configuration at a temperature above the critical temperature while attached to the teeth in the patient's mouth.

7. In a combination as set forth in claim 6,
the strands being braided in a one-on-one configuration.

8. In a combination as set forth in claim 6,
the strands being braided in a two-on-one configuration.

9. In a combination as set forth in claim 6,
there being at least three (3) strands in the filament.

10. In combination for resetting the position of teeth in a patient's mouth to a particular configuration,
a plurality of strands made from a material having a composition of substantially fifty five percent (55%) titanium and forty five percent (45%) nickel,
the plurality of strands being disposed in a braided relationship having a hollow central opening,
a wire extending through the opening defined by the plurality of strands,
the wire and the plurality of strands defining a filament,
the filament having properties of being formed to the particular configuration at a particular elevated temperature, of being bent easily to any other configuration than the preset configuration at a critical temperature below the particular elevated temperature in accordance with the disposition of the teeth in the patient's mouth, of being coupled to the patient's teeth in such other configuration and of returning to the particular configuration in the patient's mouth.

11. In a combination as set forth in claim 10,
the other configuration corresponding to the configuration of the teeth in the patient's mouth.

12. In a combination as set forth in claim 10,
the wire being made from a material selected from the group consisting of stainless steel, a titanium molybdenum alloy and an alloy of substantially fifty five percent (55%) titanium and forty five percent (45%) nickel.

13. In a combination as set forth in claim 12,
the plurality of strands being formed in a two-on-one relationship.

14. In combination for resetting the position of teeth in a patient's mouth to a particular configuration, a plurality of strands disposed in a braided relationship, each of the strands being formed from a material having fifty five percent (55%) titanium and forty five percent (45%) nickel by weight, the strands being disposed to define a hollow center, a wire extending through the hollow center defined by the plurality of strands, the plurality of strands and the wire defining a multi-strand filament, the multi-strand filament having properties of being formed at a particular elevated temperature to the particular configuration, of being bent form the particular configuration at a critical temperature below the particular temperature in accordance with the actual disposition of the teeth in the patient's mouth, of being attached to the patient's teeth in the bent configuration and of returning to the particular configuration while attached to the teeth in the patient's mouth.

15. In a combination as set forth in claim 14, the wire being formed from a material selected from the group consisting of stainless steel, a titanium molybdenum alloy and an alloy of substantially fifty five percent (55%) titanium and forty five percent (45%) nickel.

16. In a combination as set forth in claim 14, the wire being made from an alloy consisting of substantially fifty five percent (55%) titanium and forty five percent (45%) nickel, and the plurality of strands being formed in a two-on-one relationship.

17. In a combination as set forth in claim 14, the plurality of strands being formed in a two-on-one relationship, the wire being made from an alloy consisting of substantially fifty five percent (55%) titanium and forty five percent (45%) nickel.

* * * * *